United States Patent [19]
Beutler et al.

[11] Patent Number: 5,925,548
[45] Date of Patent: Jul. 20, 1999

[54] MODIFIED RECEPTORS THAT CONTINUOUSLY SIGNAL

[75] Inventors: Bruce A. Beutler; Flavia M. Bazzoni, both of Dallas, Tex.

[73] Assignee: Board of Regents, The University of Texas System, Austin, Tex.

[21] Appl. No.: 08/762,308

[22] Filed: Dec. 9, 1996

Related U.S. Application Data

[63] Continuation of application No. 08/224,593, Apr. 5, 1994, abandoned.

[51] Int. Cl.$^6$ .................................................. C12N 15/00
[52] U.S. Cl. .................... 435/69.7; 435/69.1; 435/320.1; 435/325; 435/375; 435/455; 530/350; 536/23.1; 536/23.5
[58] Field of Search ........................... 530/350; 536/73.5, 536/23.1; 435/325, 375, 69.1, 69.7, 172.3, 320.1, 455

[56] References Cited

FOREIGN PATENT DOCUMENTS

WO92/10591  6/1992  WIPO.
WO92/15322  9/1992  WIPO.
WO93/23550  11/1993 WIPO.

OTHER PUBLICATIONS

Chen and Okayama, "High Efficiency Transformation of Mammalian Cells by Plasmid DNA," *Molecular and Cellular Biology*, 7(8) :2745–2752, 1987.
Digel et al., "Receptors for Tumor Necrosis Factor on Neoplastic B Cells From Chronic Lymphocytic Leukemia Are Expressed In Vitro but Not In Vivo", *Blood*, vol. 76, No. 8, 1607–1613, 1990.
Kolls et al., "Prolonged and effective blockade of tumor necrosis factor activity through adenovirus–mediated gene transfer," *Proc. Natl. Acad. Sci. USA*, 91:215–219, 1994.
Li et al., "Activation of cell growth by binding of Friend spleen focus–forming virus gp55 glycoprotein to the erythropoietin receptor," *Nature*, 343:672–764, 1990.
Longmore et al., "An Activating Mutation in the Murine Erythropoietin Receptor Induces Erythroleukemia in Mice: A Cytokine Receptor Superfamily Oncogene", *Cell*, vol. 67, 1089–1102, 1991.
Ohashi et al., "Ligand–induced activation of chimeric receptors between the erythropoietin receptor and receptor tyrosine kinases", *Proc. Natl. Acad. Sci. USA*, vol. 91, 158–162, 1994.
Schall et al., "Molecular Cloning and Expression of a Receptor for Human Tumor Necrosis Factor,"*Cell*, 61:361–370, 1990.
Smith et al., "A Receptor for Tumor Necrosis Factor Defines an Unusual Family of Cellular and Viral Proteins," *Science*, 248:1019–1023, 1990.
Souyri et al., "A Putative Truncated Cytokine Receptor Gene Transduced by the Myeloproliferative Leukemia Virus Immortalizes Hematopoietic Progenitors", *Cell*, vol. 63, 1137–1147, 1990.
Engelmann et al 1990 J Biol Chem 265(24): 14497–14504.
Dembic et al 1990 Cytokine 2(4): 231–237.
Smith et al 1987 J Biol. Chem 262(15): 6951–6954.
Smith et al 1989 J Biol Chem 264(25): 14646–14652.
Bazzoni et al 1994 Clin. Res 42(2): 113 A.
Hsu et al 1993 J Biol Chem 268(22): 16430–16436.
Goodwin et al 1991 Mol. Cell Biol 11(6): 3020–3026.
Beutler et al., "Unraveling Function in the TNF Ligand and Receptor Families," *Science* 264:667–668, Apr. 1994.
Longmore et al., "An activating mutation in themurine Erythropoietin receptor induces erythroleukemia in mice: a cytokine receptor superfamily oncogene," *Cell* 67:1089–1102, 1991.
International Search Report, Aug. 4, 1995.

*Primary Examiner*—Lila Feisee
*Assistant Examiner*—Eliane Lazar-Wesley
*Attorney, Agent, or Firm*—Arnold, White & Durkee

[57] ABSTRACT

Engineered cell surface receptors are described that are constitutively active in the absence of the cytokine, hormone or molecule that normally activates the receptor. Receptors that constitutively signal are generally created by engineering the receptor to form multimers at the cell surface. Disclosed are various DNA, protein and cellular compositions and methods of making and using such constitutively active receptors. Particular examples are fusion proteins in which the stem, transmembrane domain and cytoplasmic domain are derived from a TNF receptor, and the extracellular, multimerizing domain is derived from an erythropoietin receptor. Transfection of such fusion protein constructs into cells is shown to result in a strong cytotoxic effect.

16 Claims, 5 Drawing Sheets

3T3 T·R CHX

FIG.1D

3T3 CHX

Epo-R (truncated)

FIG. 5A

Epo/TNF-R (55kDa)

FIG. 5B

Epo/TNF-R (75kDa)

FIG. 5C

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:1:

CGTGGTACCT GAGCTTCCTG AAGCTAGGGC                                    30

(2) INFORMATION FOR SEQ ID NO:2:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:2:

GGACCTAAGC TTAGGGTCCA GGTCGCTAGC GGT                                33

(2) INFORMATION FOR SEQ ID NO:3:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:3:

GGACCTAAGC TTCCTCCGCT TGCAAATGTC ACA                                33

(2) INFORMATION FOR SEQ ID NO:4:

(i) SEQUENCE CHARACTERISTICS:
          (A) LENGTH: 34 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:4:

GCTCTAGAGC TTATCGCGGG AGGCGGGTCG TGGA                               34

(2) INFORMATION FOR SEQ ID NO:5:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:5:

```
GGACCTAAGC TTCCAAGCAT CCTTACATCG TTG                              33

(2) INFORMATION FOR SEQ ID NO:6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GCTCTAGATC AGGCCACTTT GACTGCAAT                                   29

(2) INFORMATION FOR SEQ ID NO:7:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:7:

Leu Glu Pro Phe Glu Leu Pro Pro
    1               5

(2) INFORMATION FOR SEQ ID NO:8:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:8:

Leu Glu Pro Phe Glu Pro Pro Ile
    1               5

(2) INFORMATION FOR SEQ ID NO:9:

(i) SEQUENCE CHARACTERISTICS:
        (A) LENGTH: 774 base pairs
        (B) TYPE: nucleic acid
        (C) STRANDEDNESS: single
        (D) TOPOLOGY: linear (xi) SEQUENCE DESCRIPTION: SEQ ID NO:9:

TGAGCTTCCT GAAGCTAGGG CTGCATCATG GACAAACTCA GGGTGCCCCT CTGGCCTCGG   60

GTAGGCCCCC TCTGTCTCCT ACTTGCTGGG GCAGCCTGGG CACCTTCACC CAGCCTCCCG  120

GACCCCAAGT TTGAGAGCAA AGCGGCCCTG CTGGCATCCC GGGGCTCCGA AGAACTTCTG  180

TGCTTCACCC AACGCTTGGA AGACTTGGTG TGTTTCTGGG AGGAAGCGGC GAGCTCCGGG  240

ATGGACTTCA ACTACAGCTT CTCATACCAG CTCGAGGGTG AGTCACGAAA GTCATGTAGC  300

CTGCACCAGG CTCCCACCGT CCGCGGCTCC GTGCGTTTCT GGTGTTCACT GCCAACAGCG  360

GACACATCGA GTTTTGTGCC GCTGGAGCTG CAGGTGACGA AGGCGTCCGG TTCTCCTCGC  420

TATCACCGCA TCATCCATAT CAATGAAGTA GTGCTCCTGG ACGCCCCGC GGGGCTGCTG  480

GCGCGCCGGG CAGAAGAGGG CAGCCACGTG GTGCTGCGCT GGCTGCCACC TCCTGGAGCA  540

CCTATGACCA CCCACATCCG ATATGAAGTG GACGTGTCGG CAGGCAACCG GGCAGGAGGG  600
```

-continued

| | |
|---|---|
| ACACAAAGGG TGGAGGTCCT GGAAGGCCGC ACTGAGTGTG TTCTGAGCAA CCTGCGGGGC | 660 |
| GGGACGCGCT ACACCTTCGC TGTTCGAGCG CGCATGGCCG AGCCGAGCTT CAGCGGATTC | 720 |
| TGGAGTGCCT GGTCTGAGCC CGCGTCACTA CTGACCGCTA GCGACCTGGA CCCT | 774 |

(2) INFORMATION FOR SEQ ID NO:10:

(i) SEQUENCE CHARACTERISTICS:
        (A) LENGTH: 1956 base pairs
        (B) TYPE: nucleic acid
        (C) STRANDEDNESS: single
        (D) TOPOLOGY: linear     (xi) SEQUENCE DESCRIPTION: SEQ ID NO:10:

| | |
|---|---|
| CCTGGTCCGA TCATCTTACT TCATTCACGA GCGTTGTCAA TTGCTGCCCT GTCCCCAGCC | 60 |
| CCAATGGGGG AGTGAGAGGC CACTGCCGGC CGGACATGGG TCTCCCCACC GTGCCTGGCC | 120 |
| TGCTGCTGTC ACTGGTGCTC CTGGCTCTGC TGATGGGGAT ACATCCATCA GGGGTCACTG | 180 |
| GACTAGTCCC TTCTCTTGGT GACCGGGAGA AGAGGGATAG CTTGTGTCCC CAAGGAAAGT | 240 |
| ATGTCCATTC TAAGAACAAT TCCATCTGCT GCACCAAGTG CCACAAAGGA ACCTACTTGG | 300 |
| TGAGTGACTG TCCGAGCCCA GGGCGGGATA CAGTCTGCAG GGAGTGTGAA AAGGGCACCT | 360 |
| TTACGGCTTC CCAGAATTAC CTCAGGCAGT GTCTCAGTTG CAAGACATGT CGGAAAGAAA | 420 |
| TGTCCCAGGT GGAGATCTCT CCTTGCCAAG CTGACAAGGA CACGGTGTGT GGCTGTAAGG | 480 |
| AGAACCAGTT CCAACGCTAC CTGAGTGAGA CACACTTCCA GTGCGTGGAC TGCAGCCCCT | 540 |
| GCTTCAACGG CACCGTGACA ATCCCCTGTA AGGAGACTCA GAACACCGTG TGTAACTGCC | 600 |
| ATGCAGGGTT CTTTCTGAGA GAAAGTGAGT GCGTCCCTTG CAGCCACTGC AAGAAAAATG | 660 |
| AGGAGTGTAT GAAGTTGTGC CTACCTCCTC CGCTTGCAAA TGTCACAAAC CCCCAGGACT | 720 |
| CAGGTACTGC GGTGCTGTTG CCCCTGGTTA TCTTGCTAGG TCTTTGCCTT CTATCCTTTA | 780 |
| TCTTCATCAG TTTAATGTGC CGATATCCCC GGTGGAGGCC CGAAGTCTAC TCCATCATTT | 840 |
| GTAGGGATCC CGTGCCTGTC AAAGAGGAGA AGGCTGGAAA GCCCCTAACT CCAGCCCCCT | 900 |
| CCCCAGCCTT CAGCCCCACC TCCGGCTTCA ACCCCACTCT GGGCTTCAGC ACCCCAGGCT | 960 |
| TTAGTTCTCC TGTCTCCAGT ACCCCCATCA GCCCCATCTT CGGTCCTAGT AACTGGCACT | 1020 |
| TCATGCCACC TGTCAGTGAG GTAGTCCCAA CCCAGGGAGC TGACCCTCTG CTCTACGAAT | 1080 |
| CACTCTGCTC CGTGCCAGCC CCCACCTCTG TTCAGAAATG GAAGACTCC GCCCACCCGC | 1140 |
| AACGTCCTGA CAATGCAGAC CTTGCGATTC TGTATGCTGT GGTGGATGGC GTGCCTCCAG | 1200 |
| CGCGCTGGAA GGAGTTCATG CGTTTCATGG GGCTGAGCGA GCACGAGATC GAGAGGCTGG | 1260 |
| AGATGCAGAA CGGGCGCTGC CTGCGCGAGG CTCAGTACAG CATGCTGGAA GCCTGGCGGC | 1320 |
| GCCGCACGCC GCGCCACGAG GACACGCTGG AAGTAGTGGG CCTCGTGCTT TCCAAGATGA | 1380 |
| ACCTGGCTGG GTGCCTGGAG AATATCCTCG AGGCTCTGAG AAATCCCGCC CCCTCGTCCA | 1440 |
| CGACCCGCCT CCCGCGATAA AGCCACACCC ACAACCTTAG GAAGAGGGAC TTGAACTTCA | 1500 |
| AGGACCATTC TGCTAGATGC CCTACTCCCT GTGGGTGAAA AGTGGGCAAA GGTCTCTAAG | 1560 |
| GGGAAGGCTC GAGCTGGTAG CCACTTCCTT GGTGCTACCA ACTTGGTGTA CATAGCTTTT | 1620 |
| CTCAGCCGCC GAGGACTGCC TGAGCCAGCC ACTTGTGAGT GGCAGGGAGA TGTACCATCA | 1680 |
| GCTCCTGGCC AGCTGAGGGT GCCAAAGACA GGATTGTAGA GGAAAGGCAC AATGTATCTG | 1740 |
| GTGCCCACTT GGGATGCACA GGGCCCAAGC CAAGCTTCTC AGGGCCTCCT CAGTGGGTTT | 1800 |
| CTGGGCCTTT TTCACTTTTG ATAAGCAATC TTTGTATCAA TTATATCACA CTAATGGATG | 1860 |
| AACTGTGTAA GGTAAGGACA AGCATAGAAA GGCGGGGTCT CCAGCTGGAG CCCTCGACTC | 1920 |

TTGTAAATAC ACTAAACGTC TAAAAATGAA AAAAAA          1956

(2) INFORMATION FOR SEQ ID NO:11:

(i) SEQUENCE CHARACTERISTICS:
        (A) LENGTH: 3796 base pairs
        (B) TYPE: nucleic acid
        (C) STRANDEDNESS: single
        (D) TOPOLOGY: linear (xi) SEQUENCE DESCRIPTION: SEQ ID NO:11:

ACTAGAGCTC CAGGCACAAG GGCGGGAGCC ACCGCTGCCC CTATGGCGCC CGCCGCCCTC          60

TGGGTCGCGC TGGTCTTCGA ACTGCAGCTG TGGGCCACCG GCACACAGT GCCCGCCCAG         120

GTTGTCTTGA CACCCTACAA ACCGGAACCT GGGTACGAGT GCCAGATCTC ACAGGAATAC         180

TATGACAGGA AGGCTCAGAT GTGCTGTGCT AAGTGTCCTC CTGGCCAATA TGTGAAACAT         240

TTCTGCAACA AGACCTCGGA CACCGTGTGT GCGGACTGTG AGGCAAGCAT GTATACCCAG         300

GTCTGGAACC AGTTTCGTAC ATGTTTGAGC TGCAGTTCTT CCTGTACCAC TGACCAGGTG         360

GAGATCCGCG CCTGCACTAA ACAGCAGAAC CGAGTGTGTG CTTGCGAAGC TGGCAGGTAC         420

TGCGCCTTGA AAACCCATTC TGGCAGCTGT CGACAGTGCA TGAGGCTGAG CAAGTGCGGC         480

CCTGGCTTCG GAGTGGCCAG TTCAAGAGCC CCAAATGGAA ATGTGCTATG CAAGGCCTGT         540

GCCCCAGGGA CGTTCTCTGA CACCACATCA TCCACTGATG TGTGCAGGCC CCACCGCATC         600

TGTAGCATCC TGGCTATTCC CGGAAATGCA AGCACAGATG CAGTCTGTGC GCCCGAGTCC         660

CCAACTCTAA GTGCCATCCC AAGGACACTC TACGTATCTC AGCCAGAGCC ACAAGATCC         720

CAACCCCTGG ATCAAGAGCC AGGGCCCAGC CAAACTCCAA GCATCCTTAC ATCGTTGGGT         780

TCAACCCCCA TTATTGAACA AAGTACCAAG GGTGGCATCT CTCTTCCAAT TGGTCTGATT         840

GTTGGAGTGA CATCACTGGG TCTGCTGATG TTAGGACTGG TGAACTGCAT CATCCTGGTG         900

CAGAGGAAAA AGAAGCCCTC CTGCCTACAA AGAGATGCCA AGGTGCCTCA TGTGCCTGAT         960

GAGAAATCCC AGGATGCAGT AGGCCTTGAG CAGCAGCACC TGTTGACCAC AGCACCCAGT        1020

TCCAGCAGCA GCTCCCTAGA GAGCTCAGCC AGCGCTGGGG ACCGAAGGGC GCCCCCTGGG        1080

GGCCATCCCC AAGCAAGAGT CATGGCGGAG GCCCAAGGGT TCAGGAGGC CGTGCCAGC         1140

TCCAGGATTT CAGATTCTTC CCACGGAAGC CACGGGACCC ACGTCAACGT CACCTGCATC        1200

GTGAACGTCT GTAGCAGCTC TGACCACAGT TCTCAGTGCT CTTCCCAAGC CAGCGCCACA        1260

GTGGGAGACC CAGATGCCAA GCCCTCAGCG TCCCCAAAGG ATGAGCAGGT CCCCTTCTCT        1320

CAGGAGGAGT GTCCGTCTCA GTCCCCGTGT GAGACTACAG AGACACTGCA GAGCCATGAG        1380

AAGCCCTTGC CCCTTGGTGT GCCGGATATG GGCATGAAGC CCAGCCAAGC TGGCTGGTTT        1440

GATCAGATTG CAGTCAAAGT GGCCTGACCC CTGACAGGGG TAACACCCTG CAAAGGGACC        1500

CCCGAGACCC TGAACCCATG GAACTTCATG ACTTTTGCTG GATCCATTTC CCTTAGTGGC        1560

TTCCAGAGCC CCAGTTGCAG GTCAAGTGAG GGCTGAGACA GCTAGAGTGG TCAAAAACTG        1620

CCATGGTGTT TTATGGGGGC AGTCCCAGGA AGTTGTTGCT CTTCCATGAC CCCTCTGGAT        1680

CTCCTGGGCT CTTGCCTGAT TCTTGCTTCT GAGAGGCCCC AGTATTTTTT CCTTCTAAGG        1740

AGCTAACATC CTCTTCCATG AATAGCACAG CTCTTCAGCC TGAATGCTGA CACTGCAGGG        1800

CGGTTCCAGC AAGTAGGAGC AAGTGGTGGC CTGGTAGGGC ACAGAGGCCC TTCAGGTTAG        1860

TGCTAAACTC TTAGGAAGTA CCCTCTCCAA GCCCACCGAA ATTCTTTTGA TGCAAGAATC        1920

AGAGGCCCCA TCAGGCAGAG TTGCTCTGTT ATAGGATGGT AGGGCTGTAA CTCAGTGGTC        1980

```
CAGTGTGCTT TTAGCATGCC CTGGGTTTGA TCCTCAGCAA CACATGCAAA ACGTAAGTAG    2040

ACAGCAGACA GCAGACAGCA CAGCCAGCCC CCTGTGTGGT TTGCAGCCTC TGCCTTTGAC    2100

TTTTACTCTG GTGGGCACAC AGAGGGCTGG AGCTCCTCCT CCTGACCTTC TAATGAGCCC    2160

TTCCAAGGCC ACGCCTTCCT TCAGGGAATC TCAGGGACTG TAGAGTTCCC AGGCCCCTGC    2220

AGCCACCTGT CTCTTCCTAC CTCAGCCTGG AGCACTCCCT CTAACTCCCC AACGGCTTGG    2280

TACTGTACTT GCTGTGACCC CAAGTGCATT GTCCGGGTTA GGCACTGTGA GTTGGAACAG    2340

CTGATGACAT CGGTTGAAAG GCCCACCCGG AAACAGCTGA AGCCAGCTCT TTTGCCAAAG    2400

GATTCATGCC GGTTTTCTAA TCAACCTGCT CCCCTAGCAT GCCTGGAAGG AAAGGGTTCA    2460

GGAGACTCCT CAAGAAGCAA GTTCAGTCTC AGGTGCTTGG ATGCCATGCT CACCGATTCC    2520

ACTGGATATG AACTTGGCAG AGGAGCCTAG TTGTTGCCAT GGAGACTTAA AGAGCTCAGC    2580

ACTCTGGAAT CAAGATACTG GACACTTGGG GCCGACTTGT TAAGGCTCTG CAGCATCAGA    2640

CTGTAGAGGG GAAGGAACAC GTCTGCCCCC TGGTGGCCCG TCCTGGGATG ACCTCGGGCC    2700

TCCTAGGCAA CAAAAGAATG AATTGGAAAG GACTGTTCCT GGGTGTGGCC TAGCTCCTGT    2760

GCTTGTGTGG ATCCCTAAAG GGTGTGCTAA GGAGCAATTG CACTGTGTGC TGGACAGAAT    2820

TCCTGCTTAT AAATGCTTTT TGTTGTTGTT TTGTACACTG AGCCCTGGCT GAGCCACCCC    2880

ACCCCACCTC CCATCCCACC TTTACAGCCA CTCTTGCAGA GAACCTGGCT GTCTCCCACT    2940

TGTAGCCTGT GGATGCTGAG GAAACACCCA GCCAAGTAGA CTCCAGGCTT GCCCCTATCT    3000

CCTGCTCTGA GTCTGGCCTC CTCATTGTGT TGTGGGAAGG AGACGGGTTC TGTCATCTCG    3060

GAAGCCCACA CCGTGGATGT GAACAATGGC TGTACTAGCT TAGACCAGCT TAGGGCTCTG    3120

CAATCAGAGG AGGGGGAGCA GGGAACAATT TGAGTGCTGA CCTATAACAC ATTCCTAAAG    3180

GATGGGCAGT CCAGAATCTC CCTCCTTCAG TGTGTGTGTG TGTGTGTGTG TGTGTGTGTG    3240

TGTGTGTGTG TGTCCATGTT TGCATGTATG TGTGTGCCAG TGTGTGGAGG CCCGAGGTTG    3300

GCTTTGGGTG TGTTTGATCA CTCTCCAGTT ACTGAGGCGG GCTCTCATCT GTACCCAGAG    3360

CTTGCACATT TTCTAGTCTA ACTTGCTTCA GGGATCTCTG TCTGCCTATG GAGTGCTCAG    3420

GTTACAGGCA GGCTGCCATA CCTGCCCGAC ATTTACATGA ATACTAGAGA TCTGAATTCT    3480

GGTCCTCACA CTTGTATACC TGCATTTTAT CCACTAAGAC ATCTCTCCAA GGGCTCCCCC    3540

TTCCTATTTA ATAAGTTAGT TTTGAACTGG CAAGATGGCT CAGTGGGTAA GGCAGTTTGC    3600

GGACAAACCT GATGACCTGA GTTGGATCCC TGACCATAAG GTAGAAGAGA CCTGATTCCT    3660

GCAAGTTGTC CTCTGACCAC CACCCCATAC ATGCTTCTGC ATATGTGCAC ACATCACATT    3720

CTTGCACACA CACTCACATA CCATAAATGT AATAAATTTT TTTAAATAAA TTGATTTTAT    3780

CTTTTAAAAA AAAAAA                                                   3796
```

MODIFIED RECEPTORS THAT CONTINUOUSLY SIGNAL

This application is a file wrapper continuation of U.S. patent application Ser. No. 08/224,593 filed Apr. 5, 1994, now abandoned.

BACKGROUND OF THE INVENTION

1. Field of the Invention

The present invention relates generally to the fields of cell surface receptors and their functions. More particularly, it concerns the generation of engineered receptor molecules that are constitutively active in the absence of the cytokine, hormone or molecule that normally activates the receptor. Disclosed are various DNA, protein and cellular compositions and methods of making and using constitutively active receptors, particularly, receptors engineered to form multimers.

2. Description of the Related Art

Cytokines are a group of peptide hormones that interact with cell surface receptors to signal specific biological effects. The tyrosine kinase receptors have a consensus tyrosine kinase sequence in the cytoplasmic domain that is involved in the signal transduction mechanism. Other types of receptors signal by mechanisms that are less well understood, although there is evidence for tyrosine phosphorylation in some receptors.

The erythropoietin receptor (EPOR) recognizes a glycoprotein hormone ligand. This hormone (erythropoietin) is required for the survival, proliferation and differentiation of committed erythroid progenitors. Other members of the cytokine family to which this receptor belongs include the receptors for hematopoietic growth factors such as interleukins, colony-stimulating factors and growth hormones. Unlike the tyrosine kinase receptors, the mode of signalling activity of these cytokine receptors is not known. However, it has been suggested that dimerization or oligomerization of these receptors plays an important role in the signal mechanism (Oyashi et al., 1994).

Previous studies have also shown that a mutation in the EPOR which converts an arginine to cysteine at position 129 confers constitutive expression and induces stable receptor homooligomers (Oyashi et al., 1994; Longmore and Lodish, 1991). Chimeric receptors have also been expressed by the same group in which the cytoplasmic and extracellular domains of the EPOR and the epidermal growth factor receptor (EGFR), a tyrosine kinase receptor, have been fused to form chimeric receptors that respond to the extracellular domain ligand by the response mechanism of the cytoplasmic domain.

Tumor necrosis factor (TNF) is a cytokine mediator which initially showed much promise as an antineoplastic agent, since the protein specifically destroys transformed cells in vitro, and causes the hemorrhagic necrosis of transplantable tumors in vivo without killing normal cells. Subsequently, however, it was demonstrated that TNF has many toxic effects in living animals. Specifically, it appears to be a central mediator of endotoxic shock. Unfortunately, this has limited the therapeutic application of TNF. No human tumor has ever been successfully treated with the protein.

All of the biological effects of TNF are mediated by two types of cell membrane receptor. The larger of these, a 75 kD glycoprotein, transduces the proliferative effect of TNF, although some cytotoxic activity may be generated through this molecule as well. The smaller receptor, a 55 kD cell surface glycoprotein, bears some homology to the larger TNF receptor in the region of the extracellular domain, but has an entirely different cytoplasmic domain. It therefore generates a different signal when activated by ligand binding. It is the 55 kD cell surface receptor that appears to be chiefly responsible for the induction of TNF-mediated cytotoxicity.

TNF is a trimeric molecule. The TNF receptors exist as a mixed population of monomers on the surface of virtually all somatic cells. TNF initiates signals through both of the two types of receptor by cross-linking three identical monomeric subunits (either three 75 kD subunits or three 55 kD subunits) on the cell surface. The juxtaposition of the monomers leads to generation of a signal through a process that is not completely understood. It is clear, however, that the cross-linking of monomers, and not the engagement of TNF per se, is the important event in signal transduction. Therefore, anti-receptor antibodies can substitute for TNF, generating an agonist signal. There still exists a need however, for a mechanism of inducing the cytotoxic TNF response without inducing the side effects that are caused by administration of TNF.

SUMMARY OF THE INVENTION

The present invention, in a general and overall sense, concerns engineered receptor molecules capable of constitutively signalling, i.e., receptors that exert or induce a biological function or reaction even in the absence of the ligand that normally induces the receptor to signal a positive response. The invention arises from the surprising discovery that the formation of multimeric receptor complexes on the extracellular surface is sufficient for transmitting a positive signal to the cytoplasmic domain of the receptors even in the absence of the cognate ligand or in the presence of a ligand that has entirely different activities. For clinical use, a ligand with minimal extraneous effects would be selected.

The receptors used in the practice of the invention are preferably cytokine receptors and have three basic parts, the extracellular domain, the cytoplasmic domain and the transmembrane domain. The extracellular domain functions to recognize and bind the ligand. Binding of the ligand induces the receptors to form dimers, trimers or higher order multimers. The presence of the multimeric receptors then transmits a signal through the transmembrane domain to the cytoplasmic domain which mediates a biological response.

The present inventor(s) has(ve) discovered that a chimeric receptor which comprises an extracellular domain that is capable of forming multimeric complexes may be joined to a cytoplasmic domain from a different receptor, and that the signal is transmitted and results in a biological response. In the examples disclosed herein, the transmembrane domain is derived from the same receptor as the cytoplasmic domain, however, it is contemplated that any of several receptor transmembrane domains would function in the chimeric receptors and would be included within the scope of the present invention. For example, the transmembrane domain may be derived from the same receptor as the extracellular domain, or it may even be derived from a different receptor than either the extracellular or cytoplasmic domain. Alternatively, the transmembrane domain may be encoded by a chemically synthesized DNA fragment based on consensus transmembrane domain sequences.

In a preferred embodiment, the present invention is a polypeptide comprising a cytokine receptor cytoplasmic domain functionally connected to an extracellular domain. The extracellular domain is capable of forming multimers and stimulating constitutive signal activity in the cytoplasmic domain. One aspect of the invention is an extracellular domain that forms multimers in the absence of any signal such as the binding of a ligand. Examples of this type of domain are the tumor necrosis factor receptor extracellular domain directly linked to the tumor necrosis factor ligand, or the mouse erythropoietin extracellular receptor which contains an arginine to cysteine mutation at position 129. It is understood that any such extracellular domain covalently complexed to the cognate ligand, or an extracellular receptor domain/antibody complex, or any extracellular domain that contains a mutation that confers the spontaneous formation of multimers would be encompassed by the present claimed invention. Other examples include, but are not limited to receptors for growth hormones and the interferons. Moreover, the extracellular domain responsible for multimer formation need not be derived from a receptor. Portions of the immunoglobulin heavy chain, influenza hemagglutinin and other proteins that multimerize, either in the extracellular compartment or within the cytosol are contemplated to be useful in the design of molecules that exhibit constitutive signalling activity.

The receptor cytoplasmic domain of the present invention determines the biological response to the signal. Any type of receptor domain that responds to the formation of multimers is an acceptable embodiment of the present invention. A preferred domain is the cytoplasmic domain of the tumor necrosis factor receptor, and more particularly, the cytoplasmic domain from the 55 kDa or the 75 kDa tumor necrosis factor receptors. Other receptors that confer different biological activities are also contemplated to be encompassed by the present claimed invention. Examples of such receptors include, but are not limited to the Fas antigen, growth hormone receptor, insulin receptor and erythropoietin receptor cytoplasmic domains.

In certain embodiments, the present invention is an expression vector construct comprising a DNA sequence encoding the amino acid sequence in accordance with SEQ ID NO:7. By an expression vector is meant a segment of DNA that comprises one or more structural genes, functionally connected to the necessary promoter/enhancer regions, ribosome binding sites and polyadenylation sites necessary for the production of polypeptide products in a cell, and preferably in a eukaryotic cell. The expression vector further comprises an origin of replication and other DNA segments necessary for its own replication in a cell.

The expression vector construct may further include a DNA segment encoding a polypeptide comprising a cytokine receptor cytoplasmic domain functionally connected to an extracellular domain as the structural gene. In this embodiment, the vector directs the expression of a chimeric receptor construct that is capable of forming multimers and conferring constitutive signal activity.

In a further embodiment, the invention is a method of inducing a cytotoxic effect in a cell. The method comprises obtaining an expression vector construct comprising a cytokine receptor with constitutive signal activity and expressing the cytokine receptor in a cell. The signal confers a cytotoxic reaction. A preferred signal activity is the tumor necrosis factor receptor activity.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 5A and FIG. 5C show apoptosis induced by transfection with the chimeric Epo\TNFR expression constructs.

DETAILED DESCRIPTION OF THE PREFERRED EMBODIMENTS

It was an objective of the disclosed studies to identify multimerizing groups that might be used to create constitutive signalling activity. Multimeric and constitutively active forms of 55 kDa and 75 kDa forms of TNF as well as TNF itself and the extracellular domain of influenza hemagglutinin were tested. Both TNF and the influenza hemagglutinin are homotrimeric proteins in their native state. Additionally, the erythropoietin receptor extracellular domain was employed as a multimerizing group, with the expectation that this protein should dimerize in the presence of erythropoietin, in view of a previously described mutant dimeric form of the receptor.

A soluble form of TNF was observed, rather than the multimerizing forms expected. Surprisingly, malignant transformation of NIH 3T3 cells transfected with an expression construct coding for a secreted, soluble variant of TNF was observed.

The use of influenza hemagglutinin as a multimerizing group did not yield detectable cell surface expression of protein when the cytoplasmic domain of the TNF receptors was attached. This was surprising since truncated variants of the influenza hemagglutinin molecule, lacking any cytoplasmic domain were expressed at the cell surface.

High levels of chimeric TNF/EpoR protein were expressed at the cell surface and constitutive signal transduction was detected through the TNF cytoplasmic domain. Erythropoietin receptor extracellular domain was successfully used not only as a multimerizing group, but also the chimeric fusion proteins were active even in the absence of added ligand.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

TNF-RECEPTOR:TNF LIGAND GENE CONSTRUCTION

This example describes the generation of a genetic construct that directs the expression of a protein in which the TNF ligand is coupled to the extracellular domain of the TNF receptor, but which does not contain a cytoplasmic domain.

From genomic DNA, the entire TNF coding sequence and introns (excluding the TNF 5'-UTR and 3'-UTR sequences) was amplified by polymerase chain-reaction (PCR). The stop-codon of the TNF gene was omitted, and the terminal codon (for leucine) was spliced to a sequence encoding the extracellular domain of the TNF 55 kD receptor beginning just above the plasma membrane in the protein sequence, and continuing through the C-terminus. An aspartic acid residue was interposed to assure the formation of a salt bridge with Lysine-11 of each subunit, permitting stable trimer formation. A cDNA clone was used for this part of the amplification.

The construct produced by recombinant PCR coded for a molecule that is exteriorized under the influence of the TNF secretory signal peptide. The molecule formed a homotrimer, based on the association of TNF monomers. The extracellular "stem" acts as a spacer, to give enough flexibility to avoid tension on the TNF trimer.

The same type of construction was applied to produce a constitutive form of the 75 kD TNF receptor. As before, the TNF gene, and the receptor cDNA, were used to produce the recombinant molecule, in which an aspartic acid residue follows the C-terminal residue of the TNF monomer. These constructions were made using mouse sequences; however, the same methodology may be straightforwardly applied to the human genes and their products. The mouse provides a useful in vivo model.

After synthesis of this construct, a frame-shift mutation was detected within the expression unit. This was expected to cause termination of the protein prior to synthesis of the cytoplasmic domain; however, as shown in Example II, biological activity was detected.

EXAMPLE II

CHARACTERIZATION OF TNF-RECEPTOR:TNF CONSTRUCT

The gene described in Example I, expressing a chimeric protein without a cytoplasmic domain, was transfected into cells in vitro. The gene was transcribed, leading to the production of high levels of chimeric messenger RNA in the cytoplasm of transfected cells.

The protein was not detected using immunostaining techniques, in which rabbit anti-mouse TNF antibody was applied to the transfected cells, followed by a washing step and application of a secondary antibody of caprine origin (goat anti-rabbit IgG) coupled to fluorescein. However, secreted TNF activity was detected in the culture medium of transfected cells employing the L-929 bioassay system. Briefly, culture medium was harvested and added at various dilutions to monolayers of L-929 cells grown at a density of 70,000 cells per well of a 96-well plate. Cycloheximide was added to the assay system at a concentration of 0.1 mg/mL. The cells were allowed to incubate for 16 hours at 37° C. in a humidified $CO_2$ incubator, after which time residual cells adherent to the plastic were stained with crystal violet and quantified by densitometry. Moreover, there was evidence that the chimeric molecule produced had biological activity, despite the frame-shift mutation. The engineered molecule, though lacking a cytoplasmic domain, caused rapid destruction of transfected NIH 3T3 fibroblasts when cycloheximide was added to the culture (FIG. 1A, FIG. 1B, FIG. 1C, and FIG. 1D). As such, the molecule still mimicked the effect of TNF itself, providing evidence that the expressed mutant protein has certain functional activities.

The presence of soluble TNF activity in the culture medium suggested that the truncated protein was a secreted product, rather than a membrane-anchored product.

EXAMPLE III

TNF-RECEPTOR:TNF CONSTRUCT ONCOGENIC ACTIVITY IN VIVO

A surprising new activity of the chimeric molecule was discovered when cells expressing the construct were administered to mice. These studies showed that the modified partial receptor:ligand molecule was highly oncogenic.

Figure 1A:
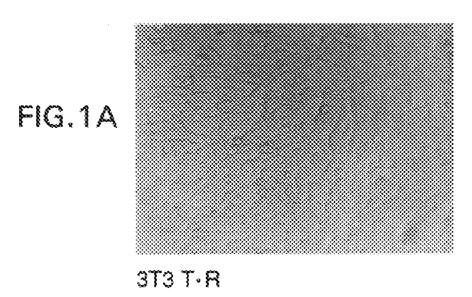
FIG. 1A. 3T3 cells transfected with the chimeric TNF receptor (T●R) expression construct, before cycloheximide treatment. Little or no morphologic change is detectable.
Figure 1B:
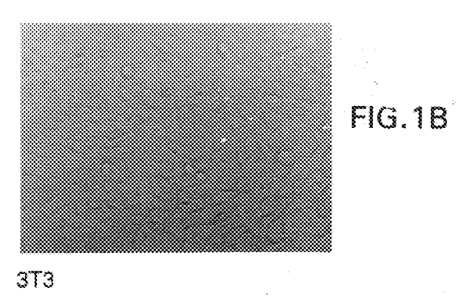
FIG. 1B. Non-transfected 3T3 cells before cycloheximide treatment. Little or no morphologic change is detectable.
Figure 1C:
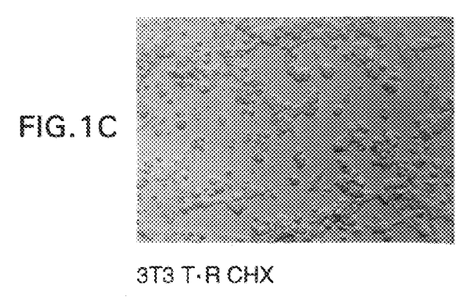
FIG. 1C. 3T3 cells transfected with the chimeric TNF receptor (T●R) expression construct, after cycloheximide treatment. Transfected 3T3 cells were treated with cycloheximide for a period of 4 hours. Note that most of the cells are lysed.
Figure 1D:
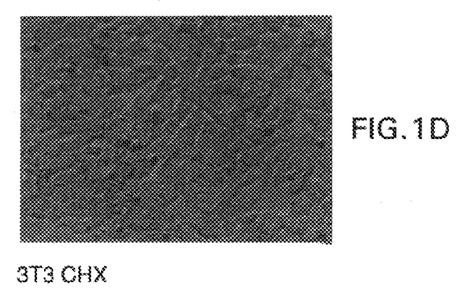
FIG. 1D. Nontransfected 3T3 cells, after cycloheximide treatment. Nontransfected cells were treated with cycloheximide for a period of 4 hours. Little or no morphologic change is detectable.
Figure 2:
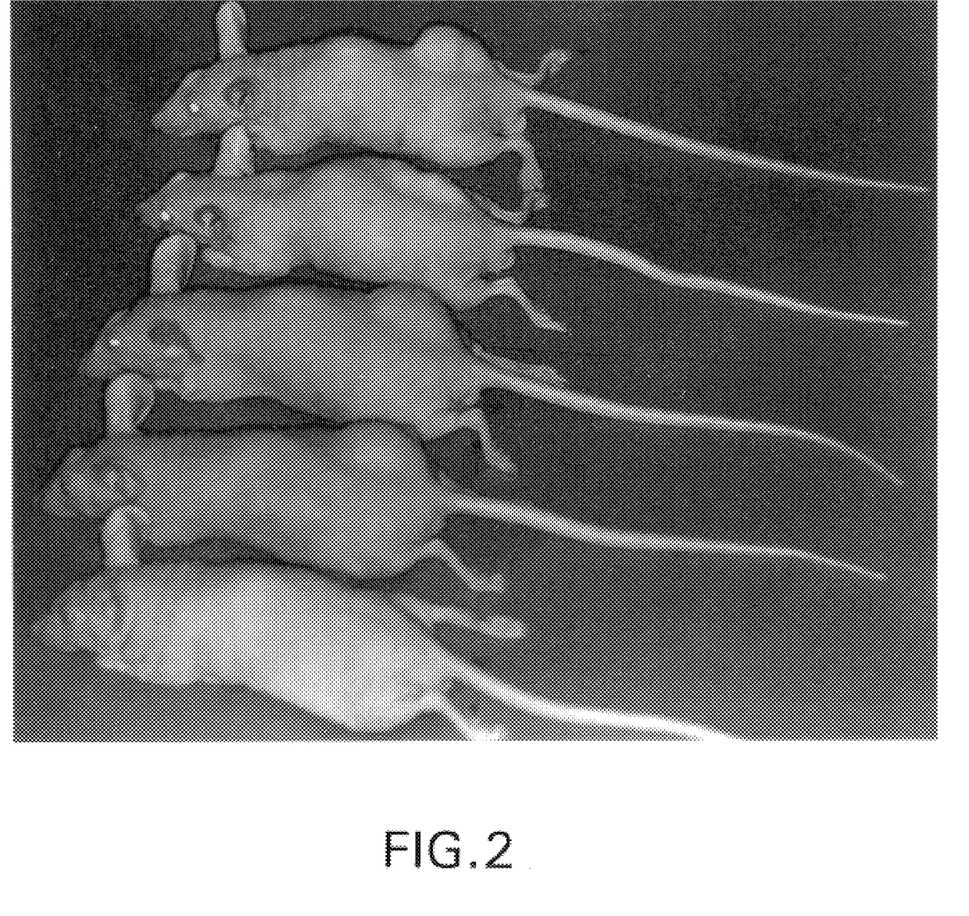
FIG. 2. Oncogenicity of the constitutively active 55 kD TNF receptor (T●R) construct. When transfected into NIH 3T3 cells, four independent clones expressing the chimeric messenger RNA were isolated and inoculated into the right flank of nude mice. These animals (the top-most four mice) developed large tumors. Animals inoculated with 3T3 cells that were transfected with an empty version of the expression vector did not develop tumors (bottom mouse in the photograph).

Even when very low levels of the chimeric messenger RNA of Example I were expressed in stably transfected NIH 3T3 cells, the cells formed large tumors in nude mice in a matter of days (FIG. 2). This phenomenon was observed in 8 out of 8 mice, inoculated with four separate clones expressing the recombinant proteins. None of the control animals (receiving cells transfected with empty vector) developed tumors. Thus, the signal generated by the recombinant protein is capable of transforming cells.

However, owing to the fact that this engineered molecule may be a secreted product, rather than a membrane-anchored product, it was not established whether the oncogenic effect is transduced by the 75 kD receptor, the 55 kD receptor, or both receptors acting in conjunction with one another.

The inventor contemplates that it is possible that certain cancers are caused by this type of rearrangement, involving the TNF receptor or other cytokine receptors, in vivo. This example provides a model for studying the formation of tumors.

EXAMPLE IV

CHIMERIC TNF RECEPTOR:HEMAGGLUTININ CONSTRUCTS

The inventor has investigated the use of a "multimerizing group" other than TNF to maintain the cytoplasmic domains in close proximity.

The influenza hemagglutinin (a trimeric protein) was first employed as the extracellular domain, on the assumption that it would maintain three cytoplasmic domains of the TNF receptors in close proximity with one another. The relevant constructs were made and expressed within COS cells. The native influenza hemagglutinin construct, as well as a construct containing only a few amino acids on the cytoplasmic side, were well expressed at the cell surface, as assessed by the ability of transfected cells to form rosettes with erythropoietin. On the other hand, the fall length construct apparently was not expressed at high levels in a native form at the cell surface, apparently because of failure to fold properly. Furthermore, no cytotoxic effect was observed on transfection of the hemagglutinin chimeras.

EXAMPLE V

CHIMERIC TNF RECEPTOR:ERYTHROPOIETIN RECEPTOR CONSTRUCTS

The next extracellular moiety investigated was the erythropoietin receptor. Fusion proteins were constructed using the erythropoietin receptor as the extracellular domain, together with the cytoplasmic domains of the two TNF receptors.

In these studies, four types of recombinant molecule were produced. The extracellular domain was derived either from the wild-type mouse erythropoietin receptor (EpoR), or from a mutant receptor in which an arginine to cysteine substitution at residue 129 results in spontaneous dimerization (Li et al., 1990). The "stem," transmembrane domain, and cytoplasmic domain of each recombinant was derived either from the 55 kD or 75 kD TNF receptor. The approach was to amplify and clone each component separately, sequence the fragments to ensure that no mutation was introduced, and then splice the fragments together using a restriction sites built into the primers used for amplification.

1. Amplifications

For the EpoR signal peptide and extracellular domain, the 5' EpoR primer used had the sequence of SEQ ID NO:1 (Kpn-I site underlined). This primer hybridizes with the 5'-untranslated region of the EpoR cDNA. The 3' EpoR primer for the EpoR signal peptide and extracellular domain had the sequence of SEQ ID NO:2 (Hind-III site underlined).

CGT GGT ACC TGA GCT TCC TGA AGC GGC (SEQ ID NO:1)

GGA CCT AAG CTT CAGG GTC CAG CTC GCT AGC GGT (SEQ 10 NO:2)

These primers were used for amplifying extracellular domains from both wild type and mutant EpoR clones (obtained from Dr. S. Watowich, Massachusetts Institute of Technology, Boston, Mass.). The mutant EpoR clone s had a mutation of arginine to cysteine at residue 129. The entire extracellular domain was amplified, encompassing the initiator methionine and continuing up to the last extracellular residue (no. 249). The amplification product encodes 24 amino acids of propeptide, plus 225 amino acids of the mature protein. The human erythropoietin receptor DNA sequence is found in Genbank, accession number J04843, SEQ ID NO:9 incorporated herein by reference.

The TNF receptor sequences are available in Genbank, as accession number M59378 (SEQ ID NO:11) for the 75 k and accession number M59377 SEQ ID NO:10) for the 55 k DNA segments, herein incorporated by reference. For the 55 kD TNF receptor "stem," transmembrane domain, and cytoplasmic domain, the 5' primer used had the sequence of SEQ ID NO:3 (Hind-III site underlined); and the 3' primer had the sequence of SEQ ID NO:4 (Xba-I site underlined; stop codon in bold).

GGA CCT AAG CTT CCT CCG CTT GCA AAT GTC ACA (SEQ ID NO:3)

GCT CTA GAG CTT ATC GCG GGA GGC GGG TCG TGG A (SEQ ID NO:4)

These primers were used for amplifying the 55 kD TNF receptor stem, transmembrane domain and cytoplasmic domain from nucleotide 687 to the stop codon at nucleotide 1460, of SEQ ID NO:10 incorporating 15 extracellular domain residues in the stem, 23 transmembrane domain residues and 219 cytoplasmic domain residues, for a total of 257 residues.

For the 75 kD TNF receptor "stem," transmembrane domain, and cytoplasmic domain, the 5' primer used had the sequence of SEQ ID NO:5 (Hind-III site underlined); and the 3' primer used had the sequence of SEQ ID NO:6 (Xba-I site underlined; stop codon in bold).

GGA CCT AAG CTT CCA AGC ATC CTT ACA TCG TTG (SEQ ID NO:5)

GCT CTA GAT CAG GCC ACT TTG ACT GCA AT (SEQ ID NO:6)

These primers were used for amplifying the 75 kD TNF receptor stem, transmembrane domain and cytoplasmic domain from nucleotide 757 to stop codon at nucleotide 1467, of SEQ ID 11 incorporating 20 extracellular domain resides in the "stem", 29 transmembrane domain residues, and 187 cytoplasmic domain residues for a total of 236 residues.

2. Cloning

All components were cloned into Bluescript-KS, and sequenced independently using the Sanger dideoxynucleotide method. The fragments were then cloned Kpn-I to Hind-III (for the EpoR coding regions) and Hind-III to Xba-I (for the TNFR coding regions) into the vector pCMV4 for expression. The full-length EpoR construct was also cloned into pCMVr for expression as a control in some studies.

For constructs containing either the wild-type or mutant EpoR domain, the predicted junctional amino acid sequences are as follows:

55 kD: . . . L-D-P-(F-E-L)-P-P- . . . (SEQ ID NO:7)

75 kD: . . . L-D-P-(F-E)-P-S-I . . . (SEQ ID NO:8)

The underlined amino acids are derived from the Epo receptor. The amino acids in parentheses are artificially introduced. The remaining amino acids represent the start of the TNF receptor moiety.

EXAMPLE VI

CHARACTERIZATION OF CHIMERIC TNF:ERYTHROPOIETIN RECEPTORS

1. Detection of Expression of Chimeric Proteins on the Plasma Membrane by Measurement of Epo Binding Radiolabeled ($^{125}I$) Epo was obtained from NEN. $2\times10^6$ COS cells were plated in a 10 cm plate, transfected according to a $CaPO_4$ method (Chen & Okayama, 1987), using 20 µg of total DNA purified by the Quiagen technique. Transfections were performed in duplicate plates, from which the cells were pooled after 12 hours. The cells were then split into triplicate wells of a six-well plate at a density of $1\times10^6$ per well. After five hours allowed for adherence to the plastic, cells were incubated on ice in 1 ml of medium containing 2% serum and 2% antibiotic mixture (pen/strep/ GIBCO), 25 mM HEPES buffer, and 0.525 pM iodinated Epo (415 nCi/ml). Incubation was allowed to continue for 2 hours with occasional gentle shaking by hand (on ice). 3 ml of ice-cold PBS containing 1 mM EDTA was then added to each well. The cells were harvested by trituration, pelleted, transferred to Eppendorf tube, and washed once more with PBS/EDTA solution (all procedures were carried out in the cold). The cell pellets were then counted for bound radioactivity.

Figure 3:
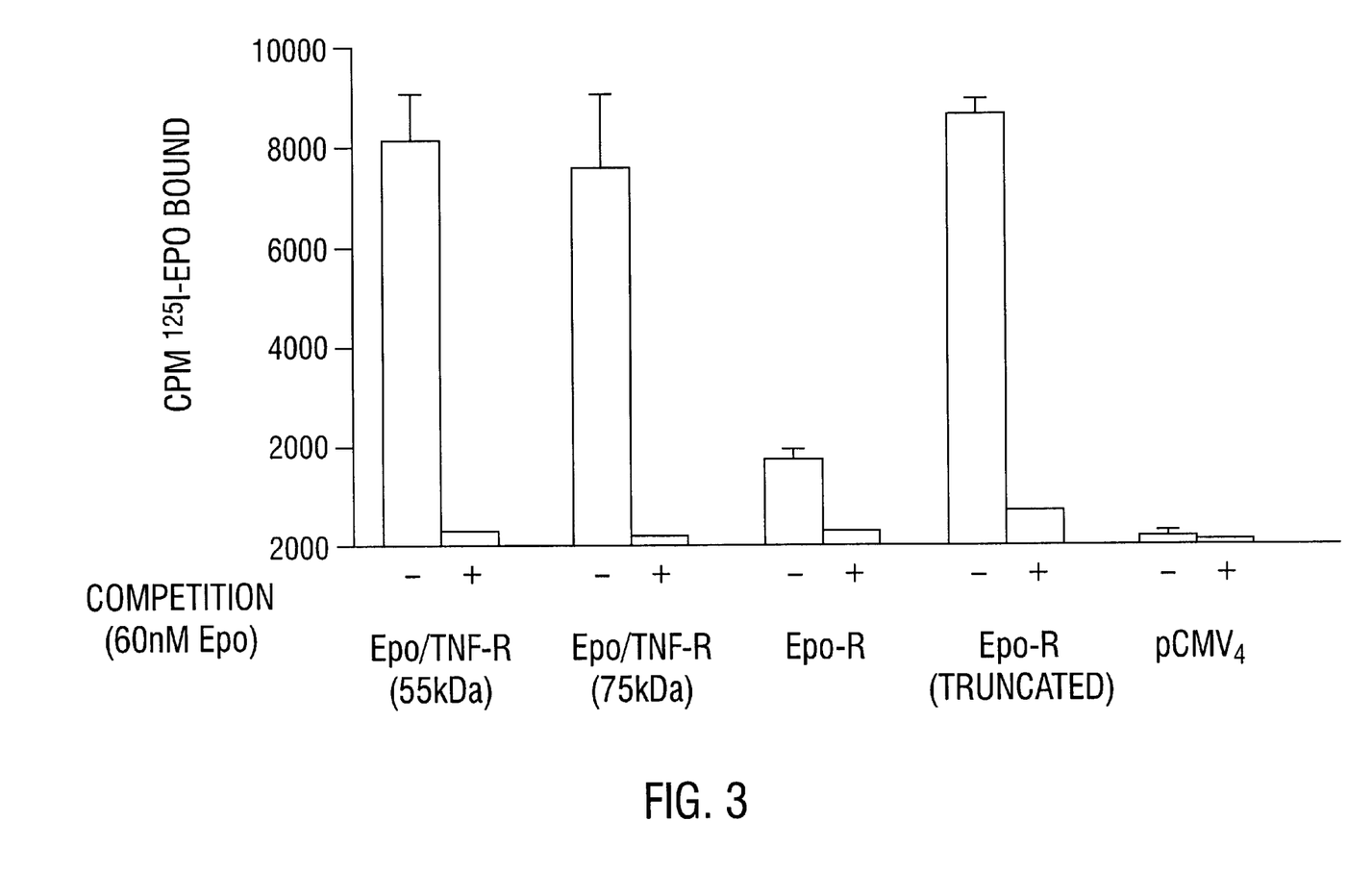
FIG. 3 shows the binding of $^{125}$-labeled Epo to chimeric, truncated, and wild-type Epo receptors expressed in COS cells following transfection with expression constructs encoding these molecules. Binding was allowed to occur in the presence (+) or the absence (−) of unlabeled Epo at a 60 nM concentration. Control cells were transfected with empty vector (pCMV4). The truncated receptor is identical to the wild-type and chimeric in the extracellular domain, except that it lacks cytoplasmic domain for signal transduction.

As illustrated in FIG. 3, transfection with the chimeric or wild-type Epo receptors led to greatly augmented Epo binding. The introduction of competing unlabeled Epo essentially abolished binding, demonstrating the specificity of the interaction. The fact that labeled Epo is capable of binding tightly and specifically to intact transfected cells indicates that the recombinant molecules are expressed on the plasma membrane of the cells. The fact that far more Epo is bound by recombinant forms of the receptor, compared with the native form of the Epo receptor, suggests that the recombinant molecules may exhibit higher affinity for the ligand, or a faster on-rate, than the native molecule. This is particularly likely in view of the fact that similar quantities of the native and recombinant receptors were expressed, as shown by immunoprecipitation studies.

2. Immunoprecipitation Studies

To further characterize the molecules that were expressed, immunoprecipitation analysis of $^{35}S$-labeled proteins was performed. $2\times10^6$ COS cells were transfected in two 10 cm plates as described above. Cells were pooled and replated as described above after 12 hours. After adherence, cells were washed in methionine/cysteine-free medium and allowed to incubate in 3 ml of the same medium for one hour. Fresh methionine/cysteine-free medium (1 ml per well), supplemented with 100 µCi of $^{35}S$ translabel (ICN), was then added to each monolayer. Cells were allowed to incubate in the presence of the label for 3 hours. They were then collected by trituration in PBS/EDTA solution.

The cells were then pelleted, and resuspended in an Eppendorf tube in 250 µl of lysis buffer (0.15 M NaCl, 50 mM tris/HCl, pH 7.4, 1 mM EDTA, and 1.0% triton X-100). Nuclei were removed by centrifugation, and the supernatants were transferred to a tube containing an equal volume of the same lysis buffer, to which 1.0% sodium deoxycholate and 0.2% SDS had been added.

Figure 4:
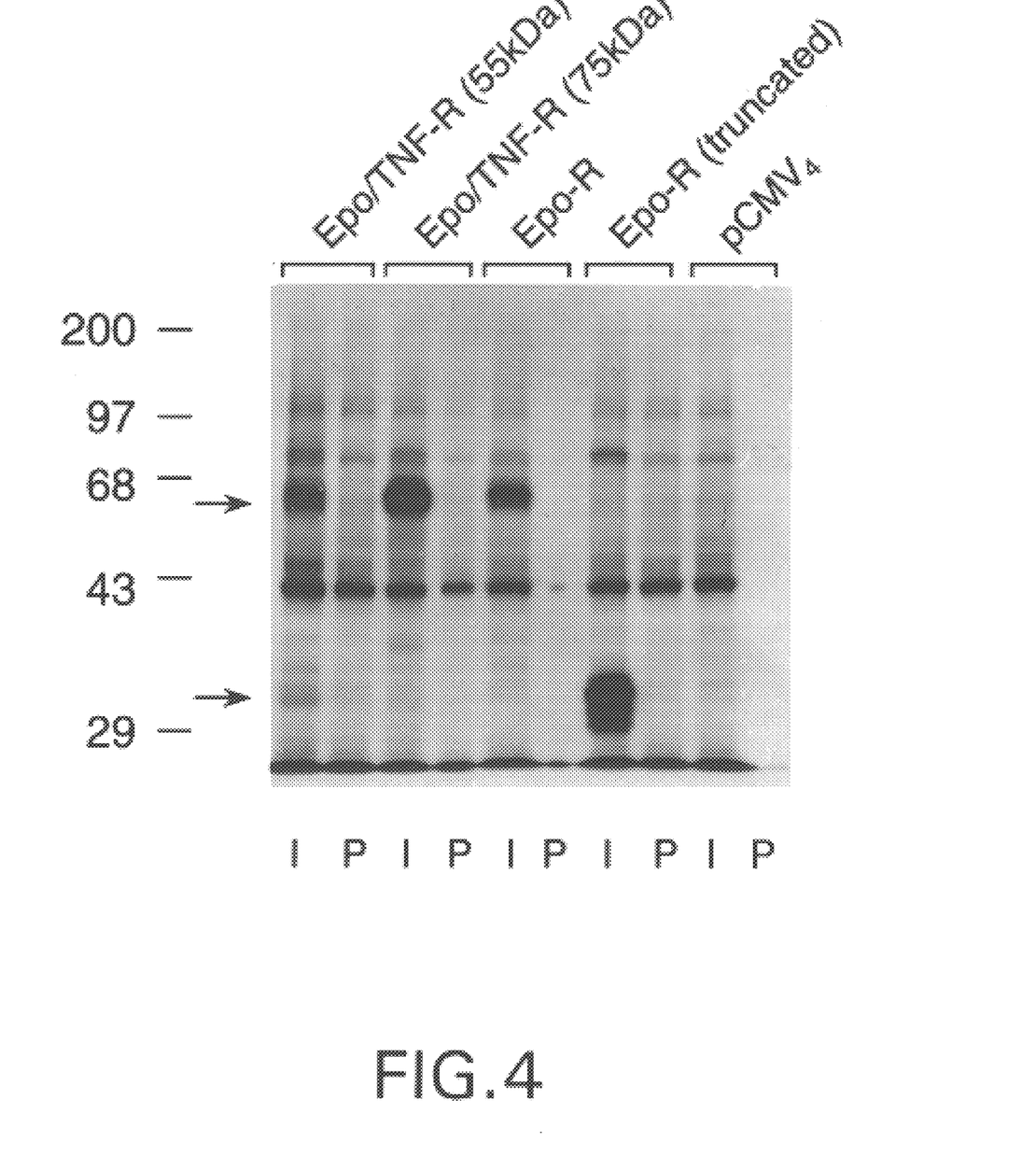
FIG. 4 shows the immunoprecipitation of Epo receptors expressed by the same COS cells described in FIG. 3 where I is the immune serum, P the pre-immune serum. The major immunoprecipitable bands representing the chimeric receptors and wild-type receptor are of the same size, approximately 60 kDa, whereas the band representing the truncated receptor is about 35 kDa, as indicated by the arrows.

Rabbit antiserum raised against the $NH_2$ terminus of the EpoR (5–10) was added at a dilution of 1:250. A non-immune serum was used as a control. Antibody was allowed to incubate overnight at 4° C. with gentle agitation. Pansorbin was then added to each tube, and allowed to react for 2 hours under the same conditions. The pansorbin was washed five times with lysis buffer, with one final wash in PBS alone (all washes on ice). The pansorbin was then resuspended in reducing SDS sample buffer, boiled, and the supernatant subjected to electrophoresis in a 10%–15% polyacrylamide gradient gel under denaturing conditions. Results are shown in FIG. 4 using $^{35}S$-labeled proteins from transfected COS cells immunoprecipitated with anti-EpoR antisera.

EXAMPLE VII

ACTIVITY OF CHIMERIC TNF:ERYTHROPOIETIN RECEPTORS

Convincing evidence of the biological activity of the chimeric TNF:EPOR proteins was also obtained from expression in mammalian cells. Cytotoxic activity was demonstrated in two ways.

First, PAM 212 cells (transformed mouse keratinocytes) were cotransfected with two vectors: pCMV5 encoding the fusion protein; and pCH110 encoding β-galactosidase at a ratio of 10:1 respectively. It was assumed that using this ratio all, or nearly all, cells transfected with the β-galactosidase vector would also be cotransfected with the expression vector encoding the fusion protein. Control cells were cotransfected with an empty pCMV5 expression vector instead of vector containing the fusion protein construct.

Figure 5A:
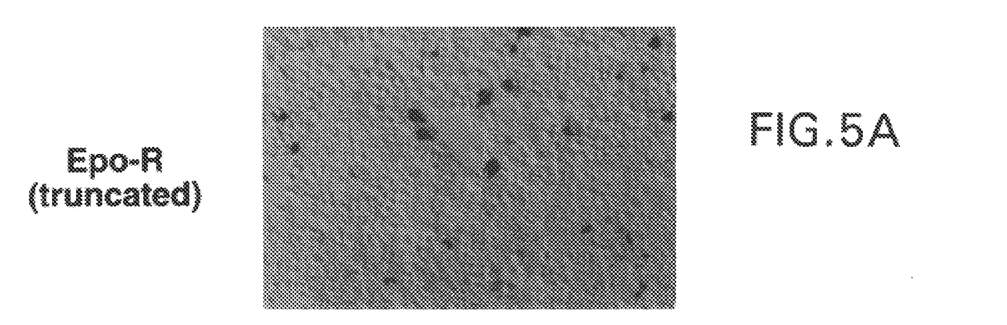
FIG. 5A shows PAM 212 cells cotransfected with a vector encoding β-galactosidase and the empty pCMV vector. Blue cells are larger and more numerous than the cells cotransfected with β-galactosidase and pCMV vectors containing either of the 55 kDa or 75 kDa chimeric receptors.
Figure 5B:
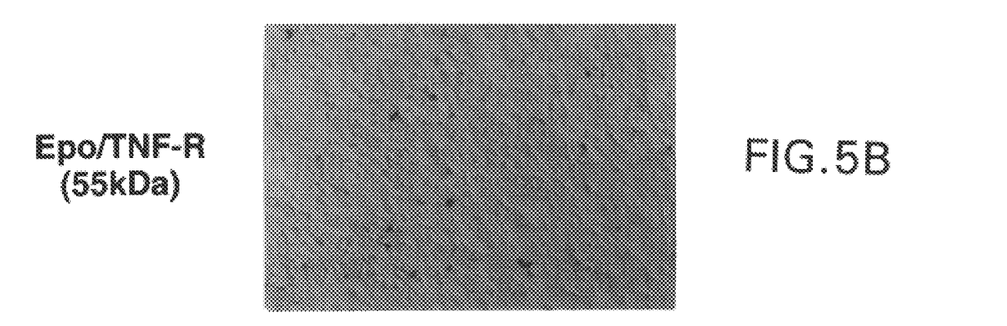
FIG. 5B shows PAM 212 cells cotransfected with β-galactosidase and the pCMV vector containing a 55 kDa chimeric receptor construct.
Figure 5C:
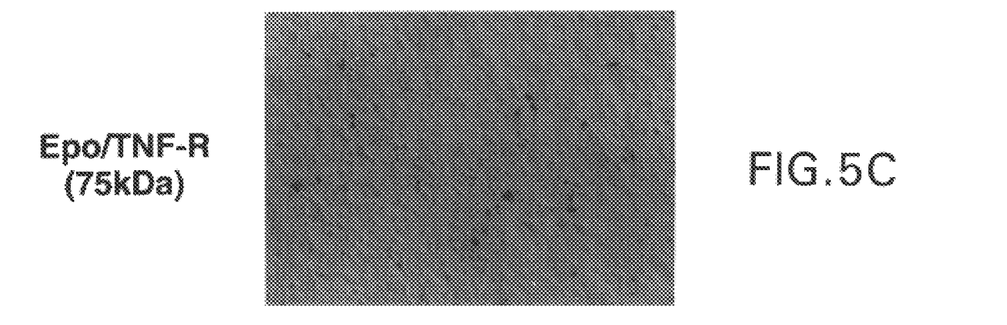
FIG. 5C shows PAM 212 cells cotransfected with a vector encoding β-galactosidase and the pCMV vector containing a 75 kDa chimeric receptor construct.

Cells thus cotransfected were stained for detection of β-galactosidase after 24 hrs and after 72 hrs, according to the method of Kolls, et al. (1994). As shown in FIG. 5A, FIG. 5B and FIG. 5C, control cultures contained abundant quantities of large, blue-staining cells at 24 and 72 hrs post transfection. Cultures cotransfected with either the 55 kDa or 75 kDa TNF receptor EPOR fusion constructs showed fewer blue cells; about ⅓ as many at 24 hrs and about 120 as many at 72 hrs. The blue-staining cells were very small, and appeared to be undergoing condensation, as typically occurs prior to TNF-induced apoptosis.

Second, NIH 3T3 cells were cotransfected with two vectors, one encoding either of the two fusion proteins; one in which the Epo receptor extracellular domain was attached to the 55 kDa or 75 kDa TNF receptor cytoplasmic domain, and the other encoding neomycin phosphotransferase (pcDNAneo) which confers resistance to the antibiotic G418. Transfection was accomplished using a ratio of ten parts fusion construct to one part pcDNAneo resistance vector. Cells were then selected for growth in the presence of G418. Cotransfection with either of the two vectors encoding fusion proteins led to a greater-than-ten-fold decrease in the number of G418 resistant colonies that formed over a two-week period of time.

Some of the surviving colonies, transfected with each of the two types of fusion construct, exhibited morphology in vitro which was suggestive of malignant transformation.

In these studies, erythropoietin was added to the cultures continuously at a concentration of 0.5 nM; however, substantially similar results were seen in the absence of added erythropoietin. The inventor had originally considered that the fusion proteins created with an erythropoietin receptor extracellular domain would be biologically inactive under normal conditions in culture, but activated by erythropoietin. Alternatively, an unusual conformation of the fusion protein may lead to dimerization in the absence of added ligand. Regardless of the mechanism, the inventor has shown that the recombinant erythropoietin receptor is active.

Surprisingly, a considerable amount of cell killing was observed following transfection with the chimeric constructs. To confirm the effect of the recombinant vector, cotransfection studies were established to determine whether fewer cells would express a reporter construct cotransfected with the chimeric expression construct than those cotransfected with an empty vector.

Transfections were performed in 293 cells, using a ratio of one part pCH110 (a β-galactosidase-encoding vector) to nine parts of chimeric EpoR encoding plasmid, or empty vector as a control. After 48 hours, cells were stained for β-galactosidase activity as described by Kolls et al., (1994).

Using the wild-type EpoR extracellular domains, fewer than 10% of the number of blue staining cells, as compared with the number in control plates, were consistently observed when cotransfected with the empty vector.

EXAMPLE VIII

FURTHER USES OF CONSTITUTIVELY ACTIVE RECEPTORS

When expressed as the products of transgenes driven by tissue specific enhancer/silencer combinations, the constitutively active receptors are contemplated for use in effectively mimicking the tissue-specific expression of TNF. At present, no system for the actual expression of TNF can achieve this, since TNF rapidly emigrates from the site of production.

The present invention also provides for the selective expression of constitutively active modified receptor conjugates in specific tissues within an animal. To achieve this, the modified receptor DNA construct is placed under the control of a cell- or tissue-specific promoter or enhancer/silencer combination, and then administered to an animal. Virtually any means of gene delivery may be employed, such as, for example, an adenoviral or retroviral vector delivery system. Whether or not many cell types receive the construct, the use of a specific genetic control element will result in only specific cells or tissues expressing the constitutively active receptor.

It is envisioned that the delivery of an engineered receptor construct, such as the one described in Example I, or Example V, to tumor cells in vivo may be used to elicit a strongly destructive effect on the tumor cells. Using cell or tissue-specific genetic control elements would mean that the lack of expression of the recombinant receptors in normal cell types would lead to low toxicity to the host. Therefore, in certain aspects the engineered receptors may be employed as effective chemotherapeutic agents for of cancer treatment. It is recognized that fusion proteins may by themselves have transforming potential. Additionally, the inventor has shown that TNF itself may have transforming activity. The selective cytotoxic action of TNF on tumor cells suggests that it might serve as an effective therapeutic agent if not for its simultaneous ability to activate neutrophils and endothelial cells, which may cause shock. It is possible that this dose-limiting toxicity might be overcome by directing the activity of TNF to the tumor cell population, to the exclusion of neutrophils, endothelial cells and other cells that actively promote an inflammatory response.

As one example, melanoma cells are often sensitive to the cytolytic effect of TNF. Melanoma cells, along with melanocytes and certain neurons, are also unique in that they express sequences placed under the control of a tyrosinase promoter. As such, the inventor contemplates creating an expression vector comprising a constitutively active TNF receptor or TNFR:EpoR receptor under the influence of the tyrosinase promoter. The administration of such a construct into an animal through the use of a viral vector, e.g., adenoviral or other vector, would result in many cells taking up the construct. However, only melanoma cells would succumb to the lethal effect of gene expression, with the melanocytes and neurons would not be expected to react to TNF-mimetic signals because no non-transformed cells are known to be killed by the direct action of TNF, even at extremely high concentrations. One might employ the insulin promoter in the therapy of insulinomas or other tumors capable of utilizing this promoter. The insulin promoter is expressed in beta-islet cells and their transformed derivatives.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Chen, C. and H. Okayama. 1987. High-efficiency transformation of mammalian cells by plasmid DNA. *Mol. Cell. Biol.* 7:2745–2752.

Kolls, J., K. Peppel, M. Silva, and B. Beutler. 1994. Prolonged and effective blockade of TNF activity through adenovirus-mediated gene transfer. *Proc. Natl. Acad. Sci.* 91:215–219.

Li, J. P., A. D. D'Andrea, H. F. Lodish, and D. Baltimore. 1990. Activation of cell growth by binding of Friend spleen focus-forming virus gp55 glycoprotein to the erythropoietin receptor. *Nature* 343:762–764.

Longmore, G. D. and H. F. Lodish. 1991. An activating mutation in the murine erythropoietin receptor induces erythroleukemia in mice: a cytokine receptor superfamily oncogene. *Cell* 67:1089–1102.

Oyashi, J., Maruyama, K., Liu, Y.-C. and A. Yoshimura. 1994. Ligand-induced activation of chimeric receptors between the erythropoietin receptor and receptor tyrosine kinases. *Proc. Natl. Acad. Sci. USA* 91:158–162.

Schall, T. J., M. Lewis, K. J. Koller, A. Lee, G. C. Rice, G. H. W. Wong, T. Gatanaga, G. A. Granger, R. Lentz, H. Raab, W. J. Kohr, and D. V. Goeddel. 1990. Molecular cloning and expression of a receptor for human tumor necrosis factor. *Cell* 61:361–370.

Smith, C. A., T. Davis, D. Anderson, L. Solam, M. P. Beckmann, R. Jerzy, S. K. Dower, D. Cosman, and R. G. Goodwin. 1990. A receptor for tumor necrosis factor defines an unusual family of cellular and viral proteins. *Science* 248:1019–1023.

What is claimed is:

1. A chimeric polypeptide encoded by a nucleic acid sequence comprising erythropoietin (EPO) receptor DNA (SEQ ID NO:9) fused with TNF receptor DNA SEQ ID NO:10 or SEQ ID NO:11.

2. The polypeptide of claim 1 wherein the EPO receptor DNA encodes amino acids 1–249 of EPO receptor DNA having Genbank accession number J04843 (SEQ ID NO:9).

3. The polypeptide of claim 1 encoded by EPO receptor DNA having Genbank accession number J04843 (SEQ ID NO:9) wherein arginine amino acid residue 129 is replaced with cysteine.

4. The polypeptide of claim 1 having a TNF receptor encoded by nucleic acid 757-1464 of SEQ ID NO:11.

5. The polypeptide of claim 1 having a TNF receptor encoded by nucleic acid sequence 687-1457 of SEQ ID NO:10.

6. The polypeptide of claim 4 that has a junctional amino acid sequence between the TNF receptor and the EPO receptor comprising amino acid sequence 1–5 of SEQ ID NO:8.

7. The polypeptide of claim 5 that has a junctional amino acid sequence between the TNF receptor and the EPO receptor comprising amino acid sequence 1–6 of SEQ ID NO:7.

8. A DNA segment encoding the chimeric polypeptide of claim 1.

9. A vector comprising a DNA segment in accordance with claim 8.

10. The vector of claim 9 wherein said DNA comprises a nucleotide sequence encoding the amino acid sequence of SEQ ID NO:7 or SEQ ID NO:8.

11. A cell transformed with the vector of claim 9.

12. The cell according to claim 11 wherein the cell is a keratinocyte.

13. The cell according to claim 11 wherein said cell is a PAM 212 cell.

14. The cell of claim 11 wherein said cell is a fibroblast cell.

15. The cell of claim 14 wherein said fibroblast cell is a 3T3 cell.

16. A method of inducing a cytotoxic effect in a cell comprising transforming a cell with a vector comprising a DNA segment that encodes the polypeptide of claim 4 and culturing said cell under conditions to allow expression of the cytotoxic polypeptide encoded by said DNA.

* * * * *